United States Patent [19]

Cioletti

[11] Patent Number: 4,762,003

[45] Date of Patent: Aug. 9, 1988

[54] MATERIAL TEST MACHINE FOR TENSION-COMPRESSION TESTS AT HIGH TEMPERATURE

[75] Inventor: Olisse C. Cioletti, Pittsburgh, Pa.

[73] Assignee: The United States Department of Energy, Washington, D.C.

[21] Appl. No.: 44,619

[22] Filed: May 1, 1987

[51] Int. Cl.$^4$ ................................................ G01N 3/10
[52] U.S. Cl. ........................................ 73/825; 73/837
[58] Field of Search ............... 73/825, 826, 816, 837; 374/49, 51, 50

[56] References Cited

U.S. PATENT DOCUMENTS

| | | |
|---|---|---|
| 3,028,754 | 4/1962 | Huyser . |
| 3,234,778 | 2/1966 | Kreglo, Jr. . |
| 4,018,080 | 4/1977 | Fletcher et al. . |
| 4,019,365 | 4/1977 | Woo . |
| 4,235,114 | 11/1980 | Mohler .............................. 73/826 X |
| 4,332,175 | 6/1982 | Krainski, Jr. .......................... 73/825 |
| 4,679,441 | 7/1987 | Johnson et al. ..................... 73/825 X |

OTHER PUBLICATIONS

McCarthy, H. A. et al. Autoclaves for metal. Journal of Physics, (GB) vol. 5, No. 8, Aug. 1972, pp. 790-792.

Primary Examiner—Jerry W. Myracle
Attorney, Agent, or Firm—William W. Randolph; Judson R. Hightower; Richard E. Constant

[57] ABSTRACT

Apparatus providing a device for testing the properties of material specimens at high temperatures and pressures in controlled water chemistries includes, inter alia, an autoclave housing the specimen which is being tested. The specimen is connected to a pull rod which couples out of the autoclave to an external assembly which includes one or more transducers, a force balance chamber and a piston type actuator. The pull rod feeds through the force balance chamber and is compensated thereby for the pressure conditions existing within the autoclave and tending to eject the pull rod therefrom. The upper end of the push rod is connected to the actuator through elements containing a transducer comprising a linear variable differential transformer (LVDT). The housing and coil assembly of the LVDT is coupled to a tube which runs through a central bore of the pull rod into the autoclave where it is connected to one side of the specimen. The movable core of the LVDT is coupled to a stem which runs through the tube where it is then connected to the other side of the specimen through a coupling member. A transducer in the form of a load cell including one or more strain gages is located on a necked-down portion of the upper part of the pull rod intermediate the LVDT and force balance chamber.

10 Claims, 2 Drawing Sheets

MATERIAL TEST MACHINE FOR TENSION-COMPRESSION TESTS AT HIGH TEMPERATURE

ORIGIN OF THE INVENTION

The invention described herein was made in the performance of work under a contract with the Department of Energy, Contract No. DE-AC11-76PN00014, and the United States government has rights in the invention pursuant to this contract.

BACKGROUND OF THE INVENTION

The present invention relates to apparatus for testing materials and more particularly to a testing machine which measures the changes occurring at a test specimen when subjected to a load at elevated temperatures and pressures.

Testing machines utilized for determining the characteristics of material specimens are well known and generally comprise apparatus for mounting the specimen in a piece of apparatus which is adapted to subject the specimen to tensional, compressional or torsional loads and measuring the dimensional changes, for example, as the load is applied under controlled conditions. More recently, it has become desirable to make such measurements within a particular type of controlled environment such as elevated temperature and/or pressure. Such apparatus requires that the specimen be placed in a closed container or housing which is capable of withstanding the conditions to which the specimen is being subjected. The loading forces which are to be applied to the specimen are externally generated, for example, by means of a piston type actuator which is coupled to the specimen through a pull rod passing into the housing through a set of seals. Additionally, measuring devices such as load cells and linear variable differential transformers are included for measuring the desired parameters during a testing procedure.

With respect to known prior art, U.S. Pat. No. 4,018,080, Fletcher, et al., entitled, "Device For Tensioning Test Specimens Within A Hermetically Sealed Chamber", for example, discloses a load cell in series with a piston located above a high temperature chamber with the piston applying a load to the specimen located within the chamber. In U.S. Pat. No. 4,019,365, Woo, entitled, "Thermo Chemical Analyzer", there is disclosed a linear variable differential transformer in series with a load column, with the load column being coupled to a test specimen mounted in a temperature chamber. The linear variable differential transformer, moreover, is mounted above the temperature chamber. Other examples of linear variable differential transformers are included in the teachings of U.S. Pat. No. 3,234,778, Kreglo, entitled, "Diletometer For Heated Specimens Under External Stress", and U.S. Pat. No. 3,028,754, Huyser, entitled, "Measurement Instrument".

While such apparatus is presumed to operate in the manner intended, certain limitations nevertheless exist, for example, the pull rod coupled between the specimen and actuator generating the load forces is often subjected to a condition where a pressure generated force tending to eject the pull rod is generated within the housing containing the specimen Present technology requires removal of the load cell, lifting the pull rod almost completely out of the housing, and assembling the new specimen to both the housing cover and the pull rod prior to reinsertion of the pull rod. This action imposes large displacement of the pull rod relative to the seals. Since non-wiped areas are involved, the seals are subjected to abrasive action tending to shorten their lifetime.

SUMMARY OF THE INVENTION

Accordingly, it is the primary object of the present invention to provide an improvement in materials testing apparatus.

It is a further object of the invention to provide an improvement in materials testing apparatus which includes an environmental chamber wherein the test specimen is located.

It is yet another object of the invention to provide an improvement in materials testing apparatus which reduces the required maintenance and repair of the apparatus.

And it is still a further object of the invention to provide an improvement in materials testing apparatus which is capable of determining the effects of chemistry, rate loading, type of loading and temperature for cyclic loading of pre-cracked specimens.

It is still another object of the invention to provide an improvement in materials testing apparatus which is capable of increasing load at a uniform rate or increasing deflection at a uniform rate so as to permit rate effect investigations.

And still yet another object of the present invention provides an improvement in materials testing apparatus which permits tension-compression testing or torsional fatigue testing to be carried out under controlled environmental conditions.

The objects of the present invention are fulfilled by providing an environmental chamber, for example, an autoclave which is capable of supporting therein a specimen to be subjected to loading forces from an external source such as a piston actuator. The loading force is coupled to the specimen within the autoclave by means of a loading column including a pull rod which passes through an opening at one end of the autoclave. The pull rod also passes through an external force balance chamber which receives a feedback pressure from the autoclave which acts upon a piston formed on the pull rod and which operates to counterbalance the force generated within the autoclave tending to eject the pull rod therefrom. A central longitudinal bore is formed in the pull rod which is adapted to provide a pressure feedback path to the force balance chamber as well as receiving a tube therethrough which couples the transformer coil assembly of a linear voltage differential transformer to one side of the specimen. The transformer core of the linear voltage differential transformer is furthermore coupled to a stem which extends through the tube into the autoclave where it is coupled to the other side of the specimen so that the displacement between two reference points can be measured by the linear voltage differential transformer. Furthermore, the upper portion of the pull rod intermediate the force balance chamber and linear voltage transformer includes a necked-down section which includes a load cell.

BRIEF DESCRIPTION OF THE DRAWINGS

The objects of the present invention and the attendant advantages thereof will become more readily apparent by reference to the following drawings wherein like numerals refer to like parts, and wherein.

DETAILED DESCRIPTION OF THE PREFERRED EMBODIMENTS

Figure 1:
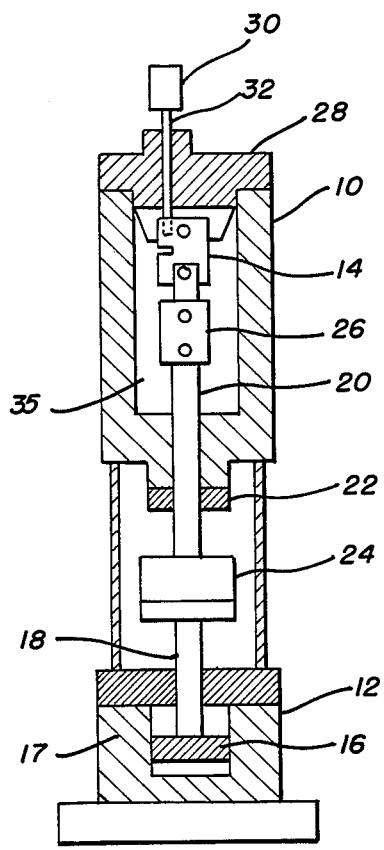
FIG. 1 is a diagrammatic view of a central longitudinal cross section of a typical prior art testing machine of the type to which the present invention is directed.

Referring now to the drawings and more particularly to FIG. 1, reference numeral 10 denotes an autoclave assembly which typically comprises a reaction vesssel, usually cylindrical in shape, which is capable of withstanding high pressure and temperature. The autoclave 10 in effect constitutes an environmental chamber for providing a means for testing material properties at high temperatures and pressures in controlled water chemistries. The autoclave 10 forms part of a materials testing machine which also includes an actuator 12 for generating loading forces which are applied to a material specimen under test 14 located in the autoclave 10. The actuator 12 is shown comprising a piston type actuator including a piston 16, piston housing 17, and piston rod 18. The piston rod 18 is coupled to a pull rod 20 which passes through the lower end cover member 22 of the autoclave 10. Typically the coupling between the pull rod 20 and the piston rod 18 is through a load cell 24, a device well known to those skilled in the art and which generates electrical output signals indicative of the stress developed in the pull rod 20 upon actuation of the piston 16. The pull rod 20 in turn is connected to the lower part of the specimen 14 by a decoupling link 26 which acts to minimize loading due to any misalignment of the elements making up the load column, including the pull rod 20, load cell 24 and piston rod 18.

Further as shown in FIG. 1, the upper portion of the autoclave assembly 10 includes an upper end cover member 28 through which a transducer element 30, typically a linear variable transformer (LVDT) couples to the specimen 14. An LVDT is a well known device which operates to generate electrical signals, with the strength of the signal induced in the secondary windings being a fuction of the position of a movable transformer or armature. The LVDT 30 of FIG. 1, for example, translates the vertical motion of the shaft 32 which is coupled to a movable transformer core, not shown, of a set of transformer windings, also not shown. In the illustrative diagram of FIG. 1, the shaft 32 passes through the upper cover member 28 to the upper part of the specimen 14.

Although not shown, the autoclave assembly 10 includes suitable seals for maintaining the environmental integrity within the internal space 35 notwithstanding any linear movement of the pull rod 20 and LVDT shaft 32.

Figure 2:
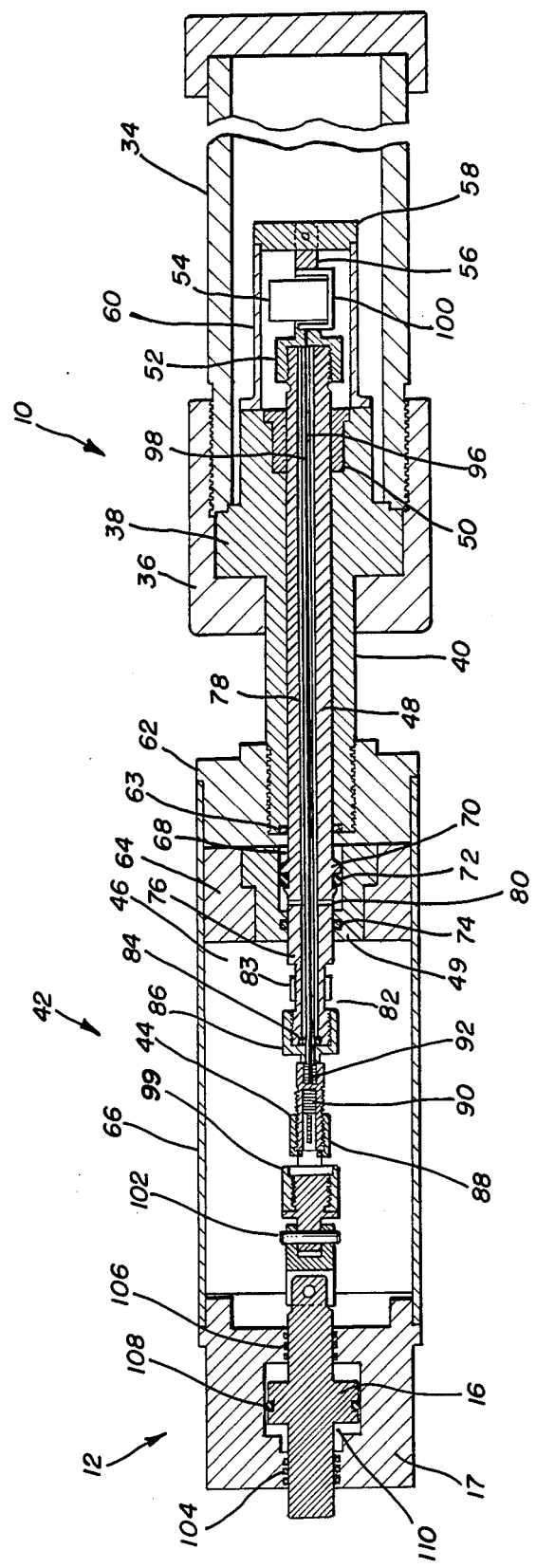
FIG. 2 is a central longitudinal cross section illustrative of the preferred embodiment of the invention.

Considering now the present invention which comprises an improvement over the type of testing apparatus shown in FIG. 1 and wherein an external actuator is coupled to the specimen residing within an autoclave type of environmental chamber, referrence is now made to FIG. 2. There, as before, reference numerals 10 and 12 generally denote an autoclave structure and actuator assembly, respectively; however, their positions are reversed. The autoclave assembly 10 of FIG. 2 is shown including a cylindrical body member 34 which has a top cover 36 attached thereto. A pull rod guide member 38 extends through the top cover 36 and has an outwardly protruding nose section 40 which connects to the lower portion of an external mechanical assembly 42. The assembly 42 includes the actuator 12, an LVDT transducer device 44, a force balance chamber 46 to be subsequently described, and associated adapter or coupling elements which make up a load column for a test specimen located in the autoclave 10.

An elongated pull rod 48 passes through the guide member 38 into the interior of the autoclave body 34 where it is held in place by an annular bearing 50. The pull rod 48 terminates and couples to a specimen adapter 52 which couples to a test specimen 54. The opposite side of the test specimen 54 is connected to a decoupling link 56 which is attached to a load bar 58. The load bar 58 in turn is held in place by means of a cylindrical reaction sleeve 60 which is secured to the bottom edge of the guide member 38.

Referring now to the assembly 42, the force balance chamber 46 is implemented in part by the upper portion of the pull rod 48 and piston housing 49. As shown in FIG. 2, the end of the nose member 40 projects into a seal nut 62 which threadably engages the upper end of the nose portion which includes a seal 63. Abutting the element 62 is an annular flange 64 which holds the piston housing 49 in place within the confines of a cylindrical sleeve type housing 66. A cavity 68 is formed in the piston housing 49 and a piston 70 is formed by an enlarged portion of the pull rod 48 and a seal 72. An upper piston seal 74 is located on the top side of the cavity 68 where it engages section 76 of the pull rod 48.

A longitudinal central bore 78 is formed in the pull rod 48 and one or more radial throughholes 80 are located above the pull rod piston 70. This permits the pressure within the body 34 of the autoclave 10 to be applied as a feedback pressure to the top side of the piston 70 providing thereby a force equal and opposite to the pressure generated within the autoclave tending to eject the pull rod 48.

Adjacent the force balance chamber 46 and the pull rod section 76, the pull rod 48 includes a necked-down region 82 for accommodating a load cell including one or more strain gages 83. The upper end of the pull rod 48 includes a bore seal 84 and pull rod 48 is coupled to the LVDT transducer 44 via a threaded adapter member 86. The LVDT 44 includes a housing 88 which is coupled to the adapter 86. Within the housing 88 is a set of fixed transformer coils 90 and a movable core or armature 92.

The preferred embodiment additionally includes a tube 96 which extends from the LVDT 44 through the length of the bore 78 of the pull rod 48 into the autoclave body 34. A stem or connecting member 98 is placed through the tube 96 where it connects at one end to the movable core or armature 92 of the LVDT and at the other end to a U-shaped mechanical coupling member 100 in the autoclave body 34 where it connects to the other side of the specimen 54.

The top part of the LVDT housing 88 couples to another adapter 99 which threadably engages a mechanical linkage 102 connected to the lower portion of the actuator piston 16. The piston 16 slidably engages upper and lower piston seals 104 and 106 of the actuator housing 17 with the piston itself having a piston seal which slidably engages the sidewall of the piston chamber 110.

In operation, actuation of the piston 16 transfers a compressional or tensional force to the specimen 54 through the loading column including the pull rod 48 and the series connected LVDT 44 with the LVDT measuring the forces on opposite sides of the specimen 54 via mechanical coupling of the specimen to the transformer coils 90 by means of the pull rod 48 and the stem 98 which couples the movable core 92 of the LVDT to the opposite side of the specimen 54 through the U-shaped mechanical coupler 100. The force balance chamber 46 meanwhile acts to counteract the forces within the autoclave 10 tending to expel the pull rod 48 by receiving a feedback pressure from the interior of the autoclave via the longitudinal bore 78 which couples to the top side of the pull rod piston 70 through the radial throughholes 80.

The structure of FIG. 2, while acting to compensate for the pressure conditions existing within the autoclave 10 and tending to expel the pull rod 48, permits the installation or removal of the test specimen 54 without the requirement of the removal of the load cell or lifting the pull rod out of the autoclave 10 as in FIG. 1 (Prior Art) which imposes a large displacement of the pull rod relative to the seals. Since non-wiped areas are involved in the FIG. 1 device, the seals are subjected to abrasive action tending to shorten their useful life. The embodiment of the present invention as disclosed does not require disassembly of the loading column in order to replace the specimen. Consequently, abrasive action on the seals of the equipment is minimized. Furthermore, access to the seals is readily accomplished without disturbing the seals that need not be replaced. This features reduces the maintenance and repair time required.

Having thus shown and described what is at present considered to be the preferred embodiment of the invention, it should be noted that the same has been made by way of illustration and not limitation. Accordingly, all modifications, alterations and changes coming within the spirit and scope of the inventiion are herein meant to be included.

What is claimed is:

1. Apparatus for testing the properties of a material specimen, comprising in combination:

a test chamber including means for mounting a test specimen therein;

actuator means coupled to said specimen located in said test chamber through a load column, said load column being further comprised of a pull rod and force transducer means serially coupled between said actuator means and said test specimen, and a force balance chamber through which said pull rod passes, located externally of said test chamber and including means responsive to the pressure inside of said test chamber and acting on said pull rod to counteract the pressure or force inside of said test chamber tending to eject said pull rod therefrom, wherein said test chamber comprises an autoclave, wherein said force balance chamber includes a piston chamber, a piston member within said piston chamber, and means for coupling the pressure inside of said autoclave to one side of said piston member, wherein said piston member comprises a portion of said pull rod, and wherein said means for coupling pressure comprises a longitudinal bore in said pull rod and at least one through-hole in said pull rod from said bore to said piston chamber.

2. The apparatus according to claim 1 and additionally including pressure seals between said piston chamber and said piston member on either side of said piston member for maintaining the integrity of pressure inside of said autoclave.

3. Apparatus for testing the properties of a material specimen, comprising in combination:

a test chamber including means for mounting a test specimen therein;

actuator means coupled to said specimen located in said test chamber through a load column, said load column being further comprised of a pull rod and force transducer means serially coupled between said actuator means and said test specimen, and a force balance chamber through which said pull rod passes, located externally of said test chamber and including means responsive to the pressure inside of said test chamber and acting on said pull rod to counteract the pressure or force inside of said test chamber tending to eject said pull rod therefrom, wherein said pull rod includes a longitudinal bore through the length of said pull rod, and additionally including means through said bore connecting said force transducer means to said test specimen.

4. The apparatus according to claim 3 wherein said test chamber comprises a pressurized chamber and additionally including a pressure seal at the outer end of said pull rod where said connecting means exits said longitudinal bore.

5. The apparatus according to claim 4 wherein said connecting means comprises an elongated tube.

6. The apparatus according to claim 5 wherein said transducer means comprises a linear variable differential transformer including a coil assembly and a movable core, said coil assembly being coupled to said tube and accordingly to one side of said test specimen, and additionally including means connecting said movable core to the other side of said test specimen through said tube.

7. The apparatus according to claim 4 wherein said pressurized chamber includes an elongated nose portion connected to said force balance chamber and having a central bore therethrough containing said pull rod.

8. The apparatus according to claim 7 and wherein said pull rod additionally includes a region of reduced thickness intermediate said force balance chamber and said transducer means for the location of a load cell thereat.

9. Apparatus for testing the properties of a material test specimen, comprising:

a test chamber including means for mounting the test specimen therein;

actuator means coupled to the test specimen for applying a test load thereto;

a load column extending between said actuator means and the test specimen for transmitting the test load to the test specimen, said load column comprising force transducer means and an elongated pull rod serially coupled between said actuator means and the test specimen, said pull rod having a longitudinal bore therethrough; and connecting means extending through the bore of said pull rod for connecting said force transducer means to the test specimen.

10. Apparatus for testing the properties of a material test specimen, comprising:

a test chamber including means for mounting the test specimen therein;

actuator means coupled to the test specimen located in said test chamber through a load column, said load column being further comprised of a pull rod and a force transducer serially coupled between said actuator means and the test specimen, said pull rod having a central bore therethrough;

a force balance chamber means connected to said test chamber and said pull rod for counteracting the pressure or force inside of said test chamber tending to eject said pull rod therefrom; and
connecting means extending through the central bore of said pull rod and connecting said force transducer to said test specimen.

* * * * *